(12) United States Patent
Gitman et al.

(10) Patent No.: US 8,434,954 B2
(45) Date of Patent: May 7, 2013

(54) HANDLE FOR WRITING INSTRUMENTS

(75) Inventors: Eliot Robert Gitman, Jerusalem (IL); David Joseph Hirsch, Jerusalem (IL)

(73) Assignee: Scalpal LLC, Wilmington, DE (US)

( * ) Notice: Subject to any disclaimer, the term of this patent is extended or adjusted under 35 U.S.C. 154(b) by 451 days.

(21) Appl. No.: 12/605,729

(22) Filed: Oct. 26, 2009

(65) Prior Publication Data

US 2010/0104344 A1 Apr. 29, 2010

Related U.S. Application Data

(63) Continuation-in-part of application No. 12/275,754, filed on Nov. 21, 2008.

(30) Foreign Application Priority Data

Jul. 10, 2008 (IL) .......................................... 192739

(51) Int. Cl.
*A46B 5/02* (2006.01)

(52) U.S. Cl.
USPC ................................................ 401/6; 16/430

(58) Field of Classification Search .............. 401/6, 131, 401/48; 16/430
See application file for complete search history.

(56) References Cited

U.S. PATENT DOCUMENTS

| | | | |
|---|---|---|---|
| D101,325 S | 3/1870 | Brown | |
| 2,782,764 A | 2/1957 | Lehman, Jr. | 120/102 |
| 4,149,811 A | 4/1979 | Coffman | 401/6 |
| D253,219 S | 10/1979 | Meyer | |
| 4,832,604 A | 5/1989 | Rusk | 434/166 |
| D307,444 S * | 4/1990 | Poisson et al. | D19/55 |
| 5,143,463 A | 9/1992 | Pozil et al. | 401/6 |
| D359,758 S * | 6/1995 | Inami | D19/55 |
| 5,440,784 A | 8/1995 | Hull et al. | |
| 5,531,754 A | 7/1996 | Shackelford, Sr. et al. | |
| 5,578,050 A | 11/1996 | Webb | |
| 5,785,443 A * | 7/1998 | Rubin | 401/6 |
| 5,975,909 A | 11/1999 | Ritchie | |
| D457,630 S | 5/2002 | Lehtonen | |
| 6,408,524 B1 | 6/2002 | Lai | |
| 6,502,314 B1 | 1/2003 | McCatty | |
| 6,554,515 B2 | 4/2003 | Debbas | 401/6 |
| D515,389 S | 2/2006 | Hsu | |
| 7,101,382 B2 | 9/2006 | George et al. | |

(Continued)

OTHER PUBLICATIONS

Office Action issued by U.S. Patent Office on May 30, 2012 in connection with corresponding parent U.S. Appl. No. 12/275,754.

(Continued)

*Primary Examiner* — David Walczak
(74) *Attorney, Agent, or Firm* — Ostrolenk Faber LLP

(57) ABSTRACT

An ergonomic writing instrument designed to facilitate the positioning of the user's hand grip. The writing instrument comprises a longitudinally extending body substantially oval in cross-section and being provided with four, substantially concave indentations positioned towards the proximal end of the handle, a first concave indentation being provided along a top surface of the handle, second and third indentations being provided along lateral surfaces, and a fourth indentation being provided along the bottom surface of the body, characterized in that the surface of the top of the handle is contoured such that extending from its distal end toward its proximal end and approaching the proximal end there is provided the concave indentation which extends and merges into an elevated ridge-like surface support which tapers angularly towards the proximal end of the handle.

8 Claims, 3 Drawing Sheets

U.S. PATENT DOCUMENTS

| | | |
|---|---|---|
| 7,150,754 B2 | 12/2006 | Ziemer |
| 7,153,317 B2 | 12/2006 | Kanodia et al. |
| D535,749 S | 1/2007 | Yaniv et al. |
| 7,357,773 B2 | 4/2008 | Watschke |
| D589,619 S | 3/2009 | Wu |
| 2002/0124353 A1 | 9/2002 | Holland-Letz |
| 2002/0170145 A1 | 11/2002 | Stvartak et al. |
| 2004/0133217 A1 | 7/2004 | Watschke |
| 2005/0150083 A1 | 7/2005 | Roberts |
| 2005/0155185 A1 | 7/2005 | Shmueli et al. |
| 2006/0026800 A1 | 2/2006 | Lawless |
| 2006/0041266 A1 | 2/2006 | Sullivan et al. |
| 2006/0075606 A1 | 4/2006 | Lawless |
| 2007/0156160 A1 | 7/2007 | Petersen |
| 2008/0051813 A1 | 2/2008 | Dunn |
| 2008/0163463 A1 | 7/2008 | Hulden |

OTHER PUBLICATIONS

Office Action issued by U.S. Patent Office on Aug. 31, 2011 in connection with corresponding parent U.S. Appl. No. 12/275,754.

Office Action issued by U.S. Patent Office on Mar. 17, 2011 in connection with corresponding parent U.S. Appl. No. 12/275,754.

Office Action issued by U.S. Patent Office on Jul. 6, 2010 in connection with corresponding parent U.S. Appl. No. 12/275,754.

Office Action issued by U.S. Patent Office on Jan. 13, 2010 in connection with corresponding parent U.S. Appl. No. 12/275,754.

* cited by examiner

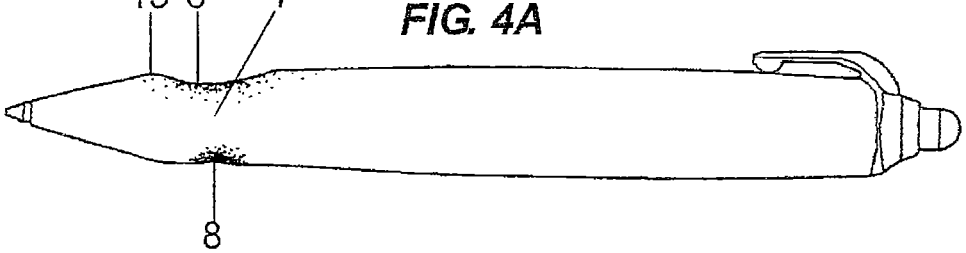
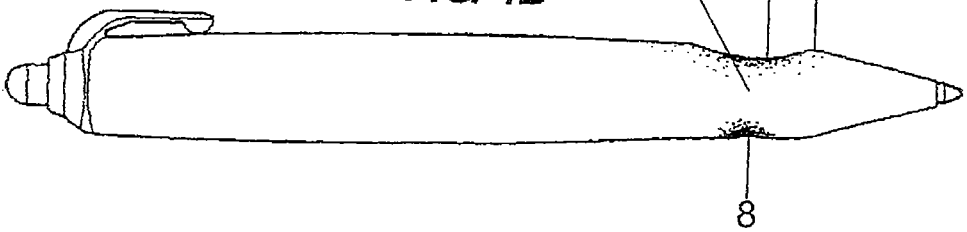
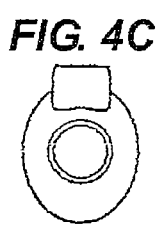
FIG. 4A
FIG. 4B
FIG. 4C
FIG. 4D
FIG. 4E
FIG. 4F

HANDLE FOR WRITING INSTRUMENTS

CROSS-REFERENCE TO RELATED APPLICATION

The present application is a continuation-in-part of application Ser. No. 12/275,754, filed Nov. 21, 2008 and entitled HANDLE FOR SURGICAL AND DENTAL TOOLS, which claims the priority of Israeli Application No. 192,739, filed Jul. 10, 2008, the disclosures of which are expressly incorporated by reference into this application.

TECHNICAL FIELD

The present invention relates to handles. More particularly, the invention relates to handles for writing instruments.

BACKGROUND OF THE INVENTION

The term "writing instruments" as used herein is intended to denote and include all writing instruments, especially those selected from the group consisting of ball point pens, felt-tipped pens, fountain pens, pencils, mechanical pencils, rapidiographs, computer stylus; scoring instruments, engraving tools, and soldering devices.

Standard writing instruments with round or octagonal gripping arrangements do not provide contoured gripping surfaces to keep the index finger, thumb and middle finger in place. Similarly, contrast writing instruments that are round or octagonal also suffer from this deficiency.

Many innovative handle designs have been implemented in order to address issues related to ergonomic requirements of grip for a writing instrument.

In U.S. Pat. No. 6,554,515, there is described and claimed an ergonomic writing instrument. However, as can be seen in FIGS. 4-8 and 18-28 of said patent, the cross-sectional configuration of said handle is substantially triangular.

Referring to U.S. Pat. Nos. 2,782,764 and 4,149,811, these patents also teach writing instruments and writing and engraving instruments, wherein the cross-sectional configuration of the handle is substantially triangular.

In U.S. Pat. No. 5,143,463, there is described and claimed a writing aid wherein the cross-sectional configuration of the handle is described as being generally pear-shaped and "provides gripping surfaces that keep the fingers in place" (page 3, line 20).

In U.S. Pat. No. 4,832,604, there is described and claimed a writing aid, including a body having a central bore for receiving a hand-held writing instrument, and an exterior including a first, second and third gripping surface. However, this adaptor sleeve is also substantially triangular in its cross-sectional configuration.

While alleviating many of the problems related to efficiently using a writing instrument, such as positioning and maintaining a desired grip, the grips disclosed in the prior art inventions do not address the need to minimize the fatigue due to the need to adjust relative position of fingers and maintain an assured operational control and alignment of the writing instrument during writing.

SUMMARY OF THE INVENTION

Therefore, the objectives of the present invention are to obviate the disadvantages of prior art writing instrument handles and to provide a writing instrument handle which has uniquely spaced indentations that accommodate finger form rather than finger pressure, thereby allowing the writing instrument to be gripped comfortably for long periods of time, and to be gripped in alternative positions.

The present invention achieves the above objectives by providing an ergonomic handle for a writing instrument, having a writing tip at its proximal end, said handle being designed to facilitate the positioning of the user's hand grip, said handle comprising a longitudinally extending body substantially oval in cross-section and being provided with four, substantially concave indentations positioned towards the proximal end of the handle, a first concave indentation being provided along a top surface of said handle, second and third indentations being provided along lateral surfaces, and a fourth indentation being provided along the bottom surface of said body, characterized in that the surface of the top of said handle is contoured such that extending from its distal end toward its proximal end and approaching said proximal end there is provided said concave indentation which extends and merges into an elevated ridge-like surface support which tapers angularly towards said proximal end of said handle, so as to allow for positioning of said user's index finger sufficiently close to said proximal end of said handle body and wherein said handle comprises a plurality of sequential ovals of varying width and shape, and wherein said indentations are positioned relative to each other to provide a contiguous interface therebetween and a contiguous interface relative to the user's thumb, index finger and middle finger to facilitate controlled rolling between the user's fingers.

In preferred embodiments of the present invention, the four indentations are spaced about 90° apart from each other.

Preferably said longitudinally extending body has an axis and said first concave indentation is cut deeper into said body towards said axis than at least one of said other indentations.

As stated hereinbefore, said writing instrument is selected from the group consisting of ball point pens, felt-tipped pens, fountain pens, pencils, mechanical pencils, rapidiographs, computer stylus; scoring instruments, engraving tools, and soldering devices.

Preferably the cross-section of segments of said handle between said ridge-like surface support and said proximal end are oval.

In preferred embodiments of the present invention, said ridge of said ridge-like surface support is positioned less than 3.0 cm from said writing tip.

In especially preferred embodiments of the present invention, said ridge of said ridge-like surface support is positioned less than 2.5 cm from said writing tip.

Preferably, said ergonomic handle is provided with a clip at its distal end wherein said clip extends less than 2 cm from said distal end towards said proximal end.

As will be realized and understood from the description of the invention hereinafter with reference to the Figures, the writing instrument of the present invention has many advantages over prior art writing instruments in that it can be held effortlessly without pressure, can be spun to give a new position, unlike standard round writing instruments. Furthermore, as described hereinafter, it can be held in at least four different positions with the user gravitating to the most comfortable position.

Referring to the preferred embodiment in which the writing instrument is provided with a clip which extends less than 2 cm., such a clip has an advantage over all existing clips in that the shorter clip works in conjunction with the ergonomic design of the pen itself and will not interfere with rotating the pen to a desired, comfortable position.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. May be shorter, longer, thicker, thinner—to adjust to different sized hands

BRIEF DESCRIPTION OF THE DRAWINGS

In the drawings:

FIG. 4A is a left side view of the handle according to the invention, showing the dorsal indentation and bottom indentation;

FIG. 4B is a right side view of the handle according to the invention, showing the dorsal indentation and bottom indentation;

FIG. 4C is the distal end view of the handle according to the invention;

FIG. 4D is the proximal end view of the handle according to the invention, showing the nib thereof;

FIG. 4E is the top view of the handle according to the invention;

FIG. 4F is the bottom view of the handle according to the invention, showing the lateral indentations.

DETAILED DESCRIPTION OF CERTAIN EMBODIMENTS OF THE INVENTION

Figure 1:
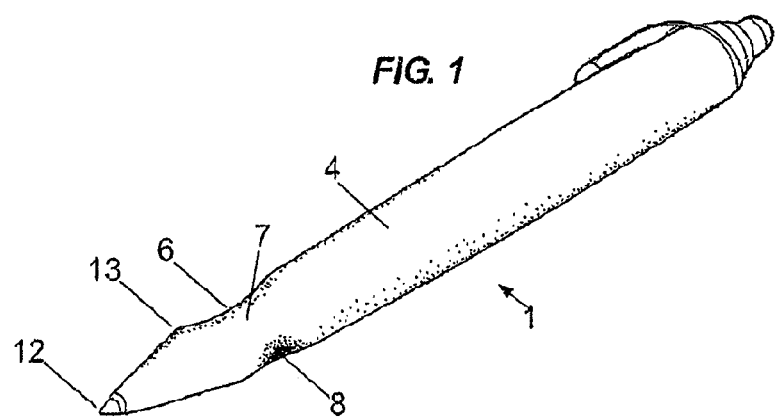
FIG. 1 is a perspective view of a preferred embodiment of the handle according to the invention.
Figure 2A:
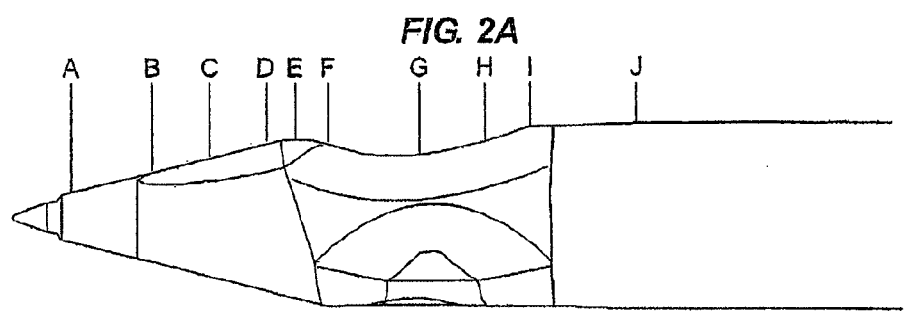
FIG. 2A is a side view of the handle and sectional views thereof.
Figure 2B:
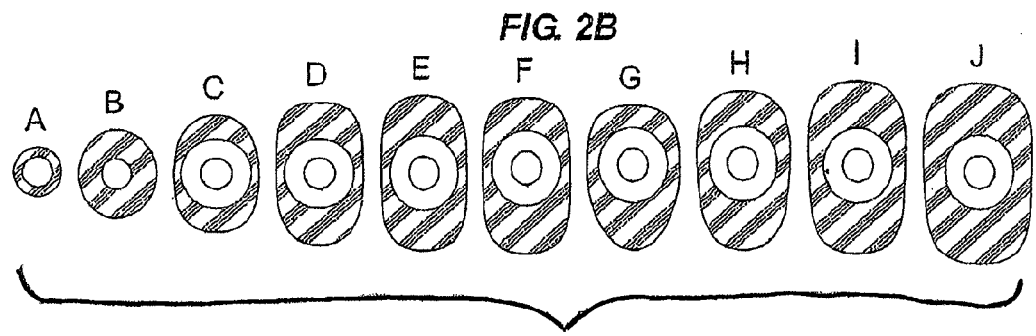
FIGS. 2B and 3 are exploded multi-sectional perspective views of the sections in FIG. 2B.
Figure 3:
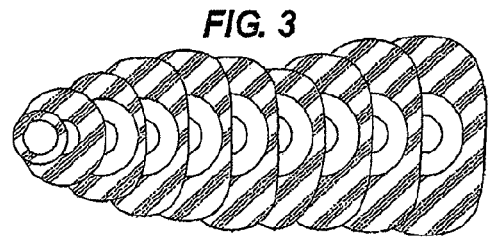

There is seen in FIG. 1 a writing instrument handle 1 comprising a longitudinally extending body 4 which is formed inter alia of sequential ovals C, D, E, F, G, H, I, J, etc., as seen in FIG. 2B, of varying width and shape. The handle 1 has four concave indentations 5 (not visible), 6, 7, and 8 moldably formed thereinto, and adjoining the proximal end of the handle 1. The first concave indentation provided along a top surface of the handle 6 extends and merges into an elevated ridge-like surface support 13. The writing instrument has a writing tip 12 at its proximal end.

According to one embodiment of the present invention, as seen with reference to FIGS. 1, 5A and 5B, the indentations 5 and 8 are designed to accommodate the side of middle finger 11, indentation 6 is designed to accommodate the index finger 9, and indentation 7 is designed to accommodate the thumb 10, as explained in the following paragraph, thereby facilitating gripping by a user. The user's fingers are free from being confined to the grip positions of the handle when in use. The general configuration of the indentations according to the present embodiment of the invention allows for the user to comfortably grip the handle 1 in various gripping positions.

Figure 5A:
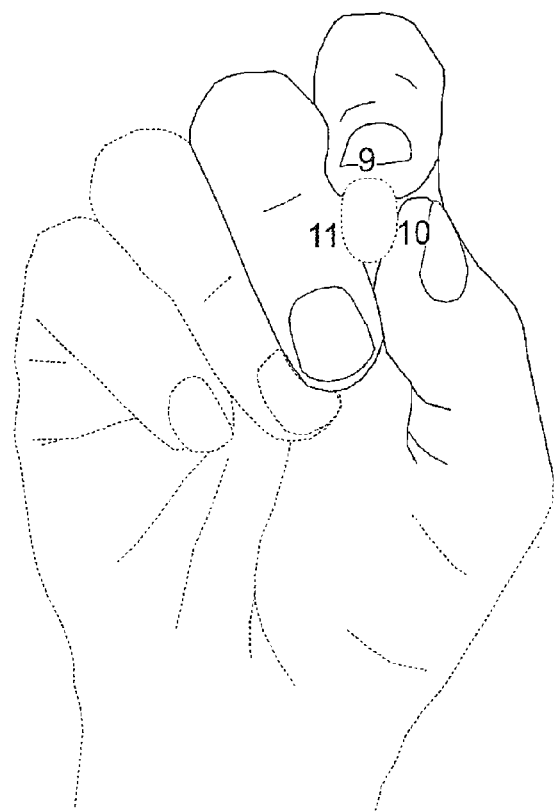
FIGS. 5A and 5B are front views of a hand holding a proposed writing instrument according to the present invention.
Figure 5B:
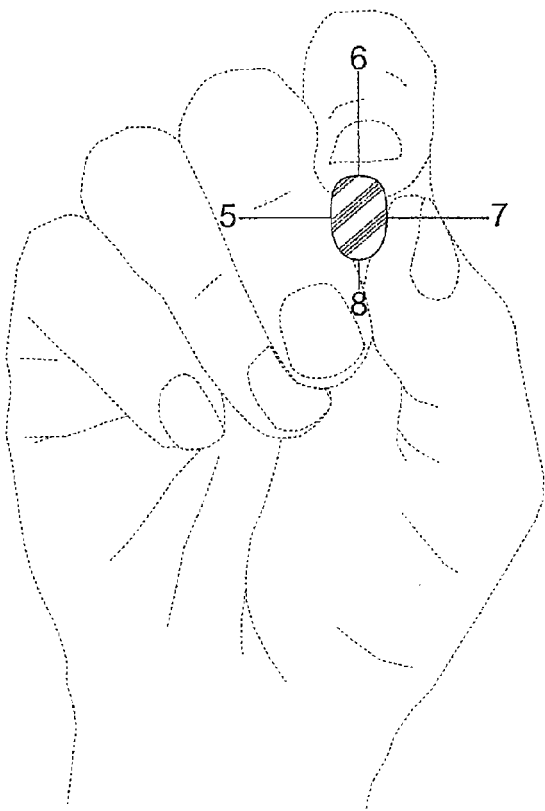

According to one embodiment of the invention, the top indentation 6 as illustrated in FIGS. 1, 4A, 4B, 5A and 5B is designed to accommodate the index finger 9 of a right handed user. The lateral indentation 7 as illustrated in FIGS. 1, 4A and 5B is designed to accommodate the thumb 10 of the user.

The bottom indentation 8 as illustrated in FIGS. 1, 4A, 4B, and 5B is designed to accommodate a portion of the middle finger 11 of the user and a portion of the thumb 10. The lateral indentation 5 as illustrated in FIGS. 4B and 5B, is designed to also accommodate a portion of the middle finger 11 of the user. The positioning of the lateral indentations is reversed in the case of a left-handed user. Thus, the accommodation of the lateral indentations for the middle finger and the thumb, involve the engagement of the same parts of the said middle finger and thumb as detailed above in respect to the right handed user.

Thus, e.g., for a standard right handed user, a first position could be with indentation 5 accommodating middle finger 11, indention 6 accommodating index finger 9, indentation 7 and 8 accommodating the thumb wherein indentation 8 also accommodates a portion of middle finger 11 as seen in FIG. 5A.

If the user finds the same to be more comfortable, he can rotate the writing instrument by 90 degrees, to obtain a second writing position wherein indentation 5 accommodates both a portion of the middle finger and the thumb, indentation 6 accommodates a further portion of the middle finger, indentation 7 accommodates the index finger and indentation 8 accommodates the thumb.

By further rotating the pen, there can be achieved a third position in which indentation 5 accommodates a portion of the thumb, indentation 6 accommodates a portion of the middle finger and a further portion of the thumb. Indentation 7 accommodates a further portion of the middle finger and indentation 8 accommodates the index finger.

With a further rotation, there is achieved a fourth position in which indentation 5 accommodates the index finger, indentation 6 accommodates a portion of the thumb, indentation 7 accommodates a portion of the middle finger and a portion of the thumb, and indentation 8 accommodates a further portion of the middle finger.

As described above and as clearly illustrated in the drawings, in the construction according to the present invention, the writing tip extends along a longitudinal and central axis which axis is substantially co-linear with the axis of the writing instrument handle body 4 which also extends longitudinally and centrally. The mentioned set of four indentations is arranged substantially around the common axis of the writing implement and its longitudinally extending handle body.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An ergonomic writing instrument, having a writing tip at its proximal end, said ergonomic writing instrument comprising a handle being designed to facilitate the positioning of the user's hand grip, said handle comprising a longitudinally extending body substantially oval in cross-section and being provided with four, substantially concave indentations positioned towards the proximal end of the handle, a first concave indentation being provided along a top surface of said handle, second and third indentations being provided along lateral surfaces, and a fourth indentation being provided along the bottom surface of said handle, characterized in that the surface of the top of said handle is contoured such that extending from a distal end toward said proximal end and approaching said proximal end there is provided said concave indentation which extends and merges into an elevated ridge-like surface support which tapers angularly towards said proximal end of said handle, so as to allow for positioning of said user's index finger sufficiently close to said proximal end of said handle body and wherein said handle comprises a plurality of sequential ovals of varying width and shape, and wherein said indentations are positioned relative to each other to provide a contiguous interface therebetween and a contiguous interface relative to the user's thumb, index finger and middle finger to facilitate controlled rolling between the user's fingers, and wherein said longitudinally extending body of said handle is elongated and has a central axis and is substantially co-linear with a corresponding longitudinal body and central axis of a writing component of said writing instrument, with said indentations being arranged around said axes of said writing instrument and the handle thereof.

2. An ergonomic writing instrument according to claim 1 wherein the four indentations are spaced about 90° apart from each other.

3. An ergonomic writing instrument according to claim 1 wherein said longitudinally extending body has an axis and said first concave indentation is cut deeper into said body towards said axis than at least one of said other indentations.

4. An ergonomic writing instrument according to claim 1 wherein said writing instrument is selected from the group consisting of ball point pens, felt-tipped pens, fountain pens, pencils, mechanical pencils, rapidiographs, computer stylus; scoring instruments, engraving tools, and soldering devices.

5. An ergonomic writing instrument according to claim 1 wherein the cross-section of segments of said handle between said ridge-like surface support and said proximal end are oval.

6. An ergonomic writing instrument according to claim 1 wherein said ridge of said ridge-like surface support is positioned less than 3.0 cm from said writing tip.

7. An ergonomic writing instrument according to claim 1 wherein said ridge of said ridge-like surface support is positioned less than 2.5 cm from said writing tip.

8. An ergonomic writing instrument according to claim 1 provided with a clip at its distal end wherein said clip extends less than 2 cm from said distal end towards said proximal end.

* * * * *